United States Patent [19]

Woolner

[11] 4,077,395

[45] Mar. 7, 1978

[54] APPARATUS FOR TAKING BLOOD SAMPLES FROM A LIVING PATIENT

[75] Inventor: Ronald Alfred Woolner, London, England

[73] Assignee: St. Thomas's Hospital Medical School, London, England

[21] Appl. No.: 731,569

[22] Filed: Oct. 12, 1976

[30] Foreign Application Priority Data

Oct. 15, 1975   United Kingdom ............... 42365/75

[51] Int. Cl.² .............................................. A61B 5/00
[52] U.S. Cl. ............................. 128/2 F; 128/DIG. 5; 141/130
[58] Field of Search ............. 128/2 F, DIG. 5, 214 R; 73/421, 425.4, 425.6; 141/130

[56] References Cited

U.S. PATENT DOCUMENTS

| | | | |
|---|---|---|---|
| 3,616,789 | 11/1971 | Grabhorn | 128/DIG. 5 |
| 3,626,929 | 12/1971 | Sanz et al. | 128/DIG. 5 |
| 3,674,011 | 7/1972 | Michel et al. | 128/2 F |
| 3,765,402 | 10/1973 | Grabhorn | 128/2 F |

*Primary Examiner*—John D. Yasko
*Attorney, Agent, or Firm*—Donald D. Jeffery

[57] ABSTRACT

A sampling apparatus is provided comprising a pump having duplex independently valved first and second inlets and a common discharge outlet, the first inlet being adapted to be connected to the vascular system of a patient via an indwelling catheter or like semi-permanent connection while the second inlet is adapted for connection to a source of normal saline. A series of collector vessels is provided for receiving fluid discharging from the pump discharge outlet. The apparatus is operated in accordance with a preselected program whereby at prescribed intervals the pump is caused to withdraw a blood sample of chosen volume through the first inlet and to discharge it to a collector vessel and thereafter to draw saline from the second inlet to flush the pump while discharging the flushings to a separate collector vessel. Preferably, the collector vessels are disposed in a rotary indexing carrier adapted to bring each collector vessel in turn into position under the pump discharge outlet.

5 Claims, 2 Drawing Figures

APPARATUS FOR TAKING BLOOD SAMPLES FROM A LIVING PATIENT

BACKGROUND OF THE INVENTION

This invention concerns the taking of blood samples from a living patient, for instance for haematological examination.

It is often necessary to take blood samples repeatedly from a patient, successive samples being taken at prescribed time intervals so that, for instance, the progress of a disease or of a treatment procedure may be monitored. Using conventional sample-taking techniques, wherein the taking of each sample is a time consuming and relatively skilled task, the taking of a regular sequence of samples at relatively short time intervals is very demanding upon the operator so that operator workloads and duty periods in a busy hospital or laboratory may often make it impracticable for samples to be taken as regularly and/or at as short intervals as might otherwise be desired. There is therefore a need for automation of the blood-taking procedure in a manner that will enable useful blood samples safely to be taken from a living patient at prescribed intervals of time and with minimum supervision by a skilled operator.

An object of the present invention is therefore to provide an apparatus capable of performing this task.

SUMMARY OF THE INVENTION

In its broadest aspect the present invention provides a sampling apparatus comprising a pump having duplex independently valved first and second inlets and a common discharge outlet, said first inlet being adapted for semi-permanent connection to the vascular system of a patient while said second inlet is adapted for connection to a source of normal saline; distributor means for effecting sequential communication between said pump discharge outlet and each of a series of collector vessels to receive fluid discharging from said outlet; and means for operating said pump, said inlet valves and said distributor means in accordance with a preselected program whereby at prescribed time intervals the pump is caused to draw a blood sample of chosen volume through said first inlet and to discharge it to an individual collector vessel and thereafter to draw saline from said second inlet to flush the pump while discharging the flushings to another collector vessel.

The said pump is preferably a peristaltic pump having a heparinised or other suitably treated pumping tube to prevent clotting, haemolysis or other degradation of blood in contact therewith, the inlet end of said tube being bifurcated, e.g. by means of a Y-piece, to provide a pair of inlet tubes extending through individual pinch valves. Desirably at least one of the inlet tubes is of a length to be suitable for semi-permanent connection to the vascular system of a patient via an indwelling catheter or like without intervening connections, thereby to minimize risk of contamination, clotting or degradation of blood drawn from the patient and that is conducted through such inlet tube. The inlet tube intended for connection to the source of saline may conveniently be part of, or be connected to, a conventional saline drip set.

The distributor means may take any convenient form: for instance if the pump discharge is flexible, as in the case of a peristaltic pump having a suitably extended pump tube, the distributor means may be arranged to cause suitable intermittent motion of the discharge over an array of stationary collector vessels so as to register with these in a prescribed sequence. However, in preferred embodiments of the invention the pump discharge is fixed in space and the distributor means comprise a rotary indexing carrier for a set of collector vessels and adapted to bring these in turn into position under the pump discharge.

While the means for operating the pump, valves and distributor means may be wholly mechanical, driving these components through suitable mechanical connections, an electromechanical system is preferred, the pump and distributor means being powered by individual electric motors and the valves being electrically-operated (e.g. solenoid valves) and the means for operating these components comprising a timing mechanism adapted to open and close the relevant operating circuits for the said components, in a prescribed, timed, sequence that is initiated at preselected times.

It will be understood that care must be taken to avoid contamination or clotting of blood drawn from the patient and for this reason the preferred operation program provides not only for flushing of the pump after discharge of a sample to a collector vessel but, thereafter, also for back flushing with saline of the first inlet, connected to the patient, so that fresh blood is drawn from the patient at the commencement of each sampling program. Thus a final stage in the preferred programme involves opening both of the inlet valves while the pump is stationary, so as to permit saline to flow reversely through the first inlet and to flush the inlet and its connecting tubing back to the patient's vascular system.

Advantageously, there may be provided a fail safe device adapted to make the sampling apparatus inoperative in the event of a malfunction of the apparatus, such as a malfunction in the timing device causing continuous withdrawal of blood from the patient. One such fail safe device comprises a series of pairs of contacts disposed adjacent the top of each collector vessel such that overfilling of a collector vessel completes the circuit between a pair of contacts which causes the sampling apparatus to stop functioning. A warning device comprising an audible signal and a flashing light may also be provided for indicating the occurrence of such malfunction of the apparatus.

The invention may be embodied in a self-contained single unit—e.g. trolley mounted and adapted to be disposed at the bedside of a patient, or it may be embodied in a multiple-patient installation for instance for an intensive care unit where the pump and valves and distributor/collector vessel components might be installed adjacent to each bedside and controlled by a centralized multiple-channel timing and control unit. A variant of the latter arrangement would be to provide self-contained bedside units with a central timing or initiating station adapted to send a starting signal to a selected unit to cause that to commence and complete a blood-taking cycle of operation.

BRIEF DESCRIPTION OF THE DRAWINGS implified view of the sampling apparatus of FIG. 1.

DESCRIPTION OF THE PREFERRED EMBODIMENT

Figure 1:
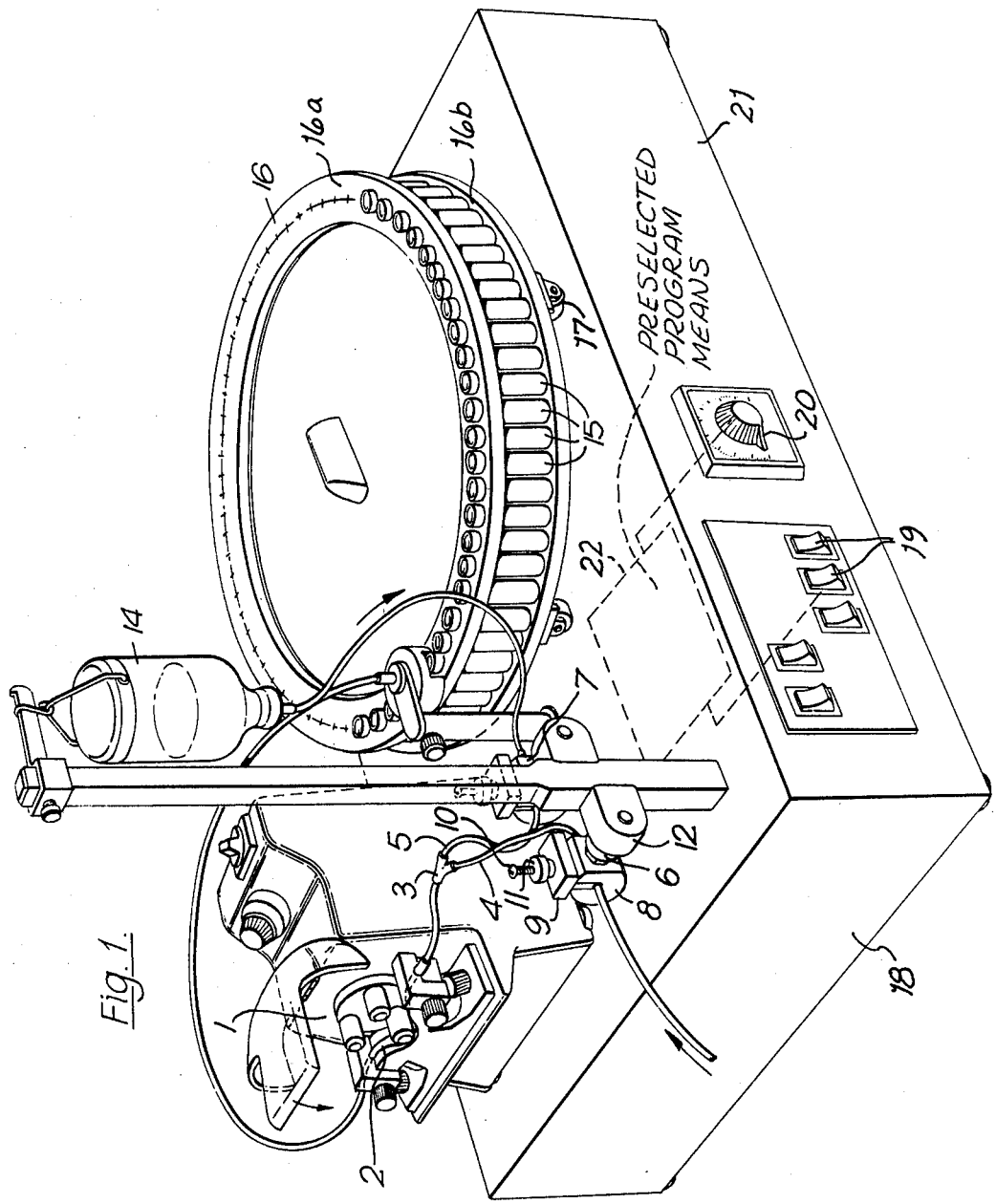

The illustrated sampling apparatus comprises a base 18 on which is mounted a peristaltic pump 1 (Watson-Marlow MHRE MK3 Flow Inducer); having a pumping tube 2 which has been heparinized and sterilized to prevent clotting, haemolysis or other degradation of blood in contact therewith. The inlet end of the pumping tube 2 is bifurcated by being provided with a Y-piece 3 attached to a pair of heparinized and sterilized tubes 4 and 5 that constitute independent inlet limbs that extend through respective solenoid pinch valves 6 and 7. Referring to FIG. 1, each valve comprises a substantially circular cylindrical block 8 having a channel extending along its axial length for receiving a respective inlet tube. The inlet tube is retained in position in the channel by a T-section clamp 9 which is held in position by a screw 10 and retaining nut 11. The valve includes a spring-loaded piston (not shown) operatable by a solenoid 12, the piston and solenoid being taken from a modified Dewrance ASCO solenoid valve, illustrated in catalog No. 8262C6V. The piston extends into the channel in block 8 and acts to clamp and close the lumen of the tube when the solenoid is not energized to withdraw the piston.

Figure 2:
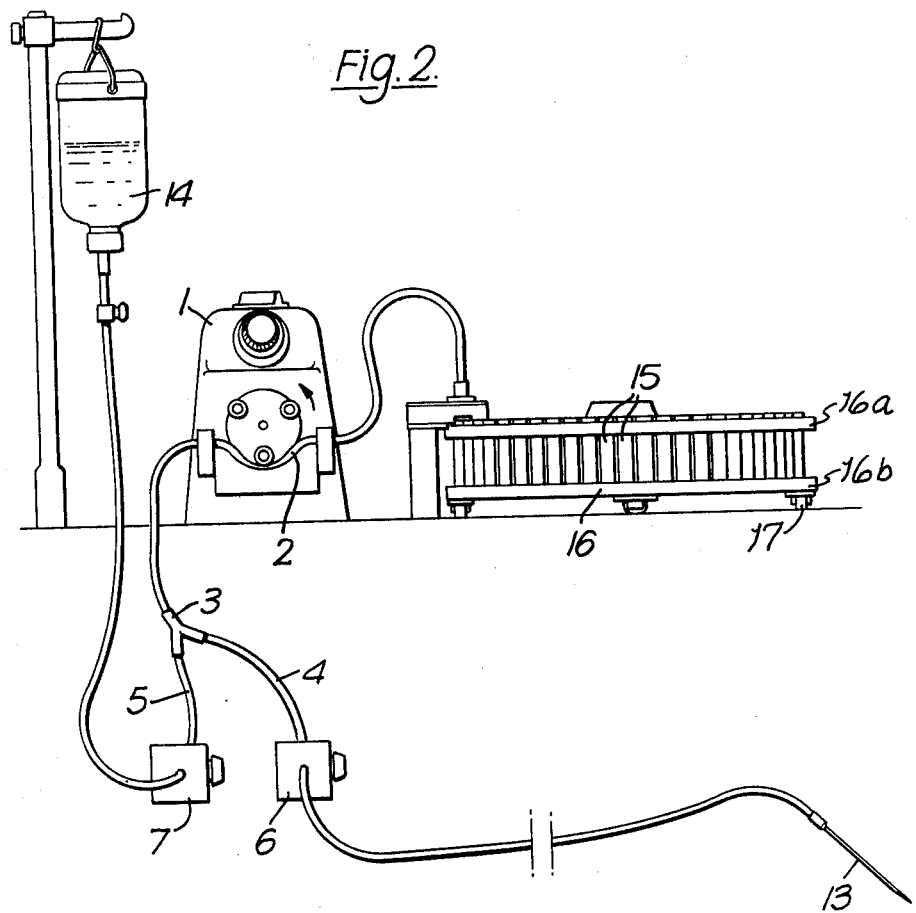

The inlet tube 4 is connected to the vascular system of a patient via an indwelling catheter 13 (FIG. 2) or like semi-permanent connection without intervening connections, thereby minimizing risk of contamination, clotting or degradation of blood drawn from the patient and conducted through the inlet tube 4. The inlet tube 5 is connected to a conventional saline drip set 14.

A rotary indexing carrier 16 is mounted on the base 18 for rotation about a centrally disposed mounting, the carrier being further supported on the base 18 by four rollers 17. The carrier 16 comprises upper and lower annular members 16a and 16b that support a series of 64 collector tubes 15 for receiving fluid discharging from the outlet end of the pumping tube 2. The carrier is controlled by a conventional indexing device (not shown) that causes the carrier to rotate intermittently to bring each collector tube in turn into position under the outlet end of the pumping tube 2.

The pump 1 and carrier 16 are powered by individual electric motors (not shown), these motors and solenoid valves 6 and 7 being operated by a variable timing device (not shown) housed within the base 18. The timing device includes a cam timer manufactured by Crouzet, the preferred timer being identified as Type 221-1, and the timer is adapted to open and close the relevant operating circuits for the said components in accordance with a preselected programme at prescribed time intervals, for example 15, 30, 45 and 60 minutes. The timing device is controllable by conventional preselected program means identified schematically at 22 in FIG. 1, with the program means being operatively coupled to control switches 19 and a timer dial 20 mounted on a front panel 21 of the base 18.

As disclosed above, the pump 1, valves 6 and 7, and program means 22, including the cam timer, are commercially available items and do not per se form part of the present invention.

In accordance with the preferred operation program of the sampling apparatus, at prescribed time intervals the pump 1 is caused to draw a blood sample of chosen volume through valve 6 and inlet tube 4 and to discharge it through the outlet end of pumping tube 2 to a first collector tube. The pump 1 is then caused to draw saline from the drip set 14 through valve 7 and inlet tube 5, and discharge it from the outlet end of pumping tube 2 to a second collector vessel, thus flushing pumping tube 2. The final stage in the operating program involves opening both valves 6 and 7 while pump 1 is stationary, so as to permit saline to flow reversely through and flush inlet tube 4, so that fresh blood is drawn from the patient at the commencement of each sampling programme.

The illustrated sampling apparatus is mounted on a movable trolley (not shown), and may thus be taken to the bedside of a patient. However, the sampling apparatus may also be embodied in a multiple-patient installation, for instance for an intensive care unit, where the pump and valves and distributor/collector vessel components are installed adjacent to each bedside and controlled by a centralized multiple-channel timing and control unit.

I claim:
1. A sampling apparatus comprising:
   (a) a pump having
      (i) duplex inlets and a common outlet
      (ii) independently operable valves controlling the respective inlets
   (b) means for connecting said first inlet to the vascular system of a patient
   (c) a source of normal saline and means for connecting said second inlet to said source
   (d) a series of collector vessels
   (e) distributor means for selectively connnecting said pump outlet to each of said collector vessels in sequence
   (f) control means for operating said pump, said inlet valves and said distributor means in accordance with a preselected program whereby at prescribed time intervals the pump is caused to draw a blood sample of chosen volume through said first inlet and to discharge it to an individual collector vessel and thereafter to draw saline from said second inlet to flush the pump while discharging the flushings to another collector vessel.

2. The samplings apparatus of claim 1 in which said pump is a peristaltic pump having a pumping tube bifurcated at its inlet end and said valves are pinch valves operable to clamp the respective limbs of said pumping tube.

3. The sampling apparatus of claim 2 in which the inlet end of said pumping tube is bifurcated by means of a Y-piece.

4. The sampling apparatus of claim 1 in which the distributor means comprises a rotary indexing carrier for a set of collector vessels and adapted to bring the collector vessels in turn into position under the pump discharge outlet.

5. The sampling apparatus of claim 1 in which said preselected program includes as a final stage back flushing with saline of the first inlet.

* * * * *